United States Patent
Brütt et al.

(10) Patent No.: US 10,309,934 B2
(45) Date of Patent: Jun. 4, 2019

(54) METHOD AND SYSTEM OF DEDUCING SOUND VELOCITY USING TIME-OF-FLIGHT OF SURFACE WAVE

(71) Applicants: Cécile Brütt, Paris (FR); Guillaume Painchaud-April, Quebec (CA); Chi-Hang Kwan, Mississauga (CA); Benoit Lepage, Quebec (CA)

(72) Inventors: Cécile Brütt, Paris (FR); Guillaume Painchaud-April, Quebec (CA); Chi-Hang Kwan, Mississauga (CA); Benoit Lepage, Quebec (CA)

(73) Assignee: OLYMPUS SCIENTIFIC SOLUTIONS AMERICAS INC, Walthan, MA (US)

( * ) Notice: Subject to any disclaimer, the term of this patent is extended or adjusted under 35 U.S.C. 154(b) by 71 days.

(21) Appl. No.: 15/472,449

(22) Filed: Mar. 29, 2017

(65) Prior Publication Data
US 2018/0284069 A1    Oct. 4, 2018

(51) Int. Cl.
| | |
|---|---|
| *G01N 29/26* | (2006.01) |
| *G01N 29/30* | (2006.01) |
| *G01N 29/06* | (2006.01) |
| *G01N 29/07* | (2006.01) |

(52) U.S. Cl.
CPC ......... *G01N 29/07* (2013.01); *G01N 29/0645* (2013.01); *G01N 29/262* (2013.01); *G01N 29/30* (2013.01); *G01N 2291/011* (2013.01); *G01N 2291/0423* (2013.01); *G01N 2291/102* (2013.01)

(58) Field of Classification Search
CPC .................. G01N 29/07; G01N 29/62; G01N 2291/0423; G01N 2291/011

USPC .......................................................... 73/597
See application file for complete search history.

(56) References Cited

U.S. PATENT DOCUMENTS

| | | | | |
|---|---|---|---|---|
| 4,462,257 | A * | 7/1984 | Gerhart ................... | G01H 11/06 310/313 B |
| 4,524,621 | A * | 6/1985 | Yamanaka ............. | G01N 29/07 73/597 |
| 5,974,889 | A * | 11/1999 | Trantow ............... | G01N 29/043 73/624 |
| 5,987,991 | A * | 11/1999 | Trantow ............. | G01N 29/2418 73/624 |
| 7,237,438 | B1 * | 7/2007 | Umbach ................ | G01N 29/07 73/597 |

(Continued)

*Primary Examiner* — Jacques M Saint Surin
(74) *Attorney, Agent, or Firm* — C. Tricia Liu; Robert Kaim (57) ABSTRACT

Disclosed is an ultrasonic non-destructive testing and inspection system and method for determining acoustic velocities in a test object. Beams of acoustic energy from firing an element of an emitting probe propagate in a first wedge, and a beam incident at the critical angle generates a surface wave in the test object. The surface wave propagates to a second wedge and signals are received at receiving elements of a receiving probe array. When a set of appropriate delays is applied to the receiving elements, the acoustic time-of-flight is the same to all receiving elements. Determination of the appropriate delays and the times-of-flight for P-type surface waves and Rayleigh surface waves enables computation of the P- and S-wave acoustic velocities in the test object. The time-of-flight measurement also enables computation of the separation between the first and second wedges.

40 Claims, 9 Drawing Sheets

(56) References Cited

U.S. PATENT DOCUMENTS

2011/0179873 A1* 7/2011 Schubert ............... G01N 29/07
                                                                             73/597

* cited by examiner

FIG. 7B

METHOD AND SYSTEM OF DEDUCING SOUND VELOCITY USING TIME-OF-FLIGHT OF SURFACE WAVE

FIELD OF THE INVENTION

The invention relates generally to ultrasonic non-destructive testing (NDT) using the techniques of full-matrix capture (FMC) and total focusing method (TFM), and more particularly to a method of using time-of-flight of surface waves to determine the ultrasound velocity in a test object.

BACKGROUND OF THE INVENTION

In a typical existing full matrix capture (FMC) acquisition, a plurality of pulser elements of one or more ultrasonic array probes are individually pulsed and an A-scan (a plot of echo response amplitude vs reception time) is received for each pulse at each of a plurality of receiver elements. The result of the acquisition is an N×M matrix of response A-scans, where M is the number of pulsers and N is the number of receivers. The existing FMC acquisition method enables full beam forming capabilities in post-processing for both emission and reception. Of all the possibilities enabled by FMC, one of the most promising aspects is the ability to provide optimized focusing at all of the imaging plane positions. This is referred to as Total Focusing Method (TFM).

In existing practice, TFM is applied by dividing the imaging volume into an array of voxels, and summing the response A-scans from the FMC matrix, with delays appropriate to the time-of-flight from each pulser via each voxel to each receiver. The term "voxel" is used herein to denote an elementary volume within the imaging volume, analogous to the term "pixel" as applied to two-dimensional images.

Figure 1A:
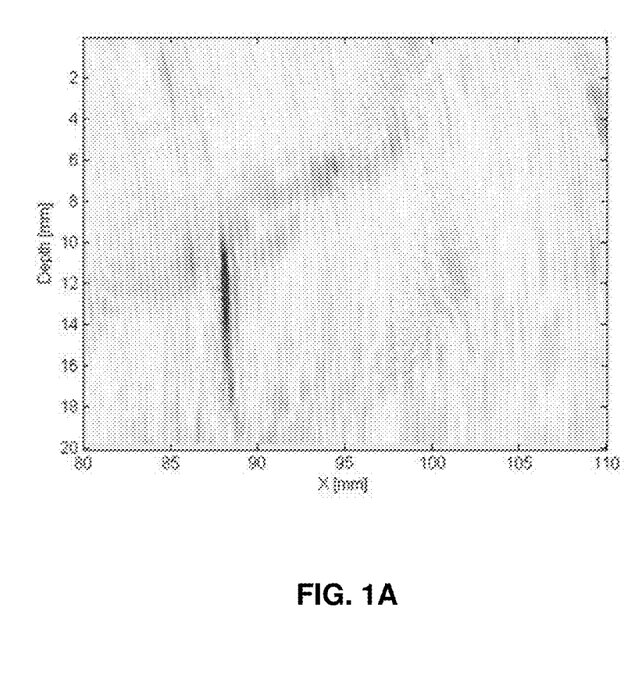
FIG. 1A is a TFM image of a flaw in a steel test object, with the image calculated assuming a S-wave velocity of 3240 m/s.
Figure 1B:
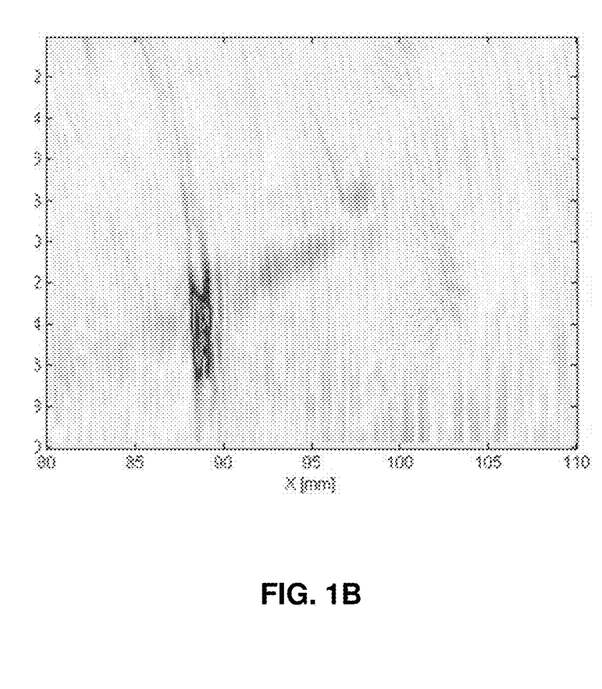
FIG. 1B is a TFM image of a flaw in a steel test object, with the image calculated assuming a S-wave velocity of 3320 m/s.

Since the calculations performed on FMC data to achieve a TFM image involve determining time-of-flight, the acoustic velocity of the relevant wave type in the test object must be known. Relevant waves types are shear waves (hereinafter referred to as S-waves) and longitudinal waves (hereinafter referred to as P-waves). A significant problem in FMC/TFM analysis is that the acoustic velocity in steel, for example, depends on the composition of the test object material, its thermal treatment and other factors that are not known when doing a non-destructive inspection. In fact, as shown in FIGS. 1A and 1B, the imaging results are extremely sensitive to the assumed sound velocity. FIGS. 1A and 1B show TFM images for a weld inspection using FMC-TFM angle beam with two probes. The image of FIG. 1A was calculated assuming a S-wave velocity of 3,240 m/s and the image of FIG. 1B was calculated assuming a S-wave velocity of 3,320 m/s. Note that there are significant differences in the images, particularly with respect to the image intensity in the vicinity of the indication.

In current practice, ultrasonic velocity measurement methods are mainly based on calculating the time necessary to reach a reflector at a given distance from the probe. However, all methods in current practice involve use of calibration blocks which by definition are not exactly the same material as the test object. Therefore the velocity measurements are necessarily imprecise with respect to the test object, and the quality of the resulting TFM images is significantly affected.

When using two probes in "pitch-catch" (P-C) mode for FMC-TFM imaging, the time-of-flight also depends on the distance between the probes. Therefore the TFM images will also sensitively depend on accurate knowledge of that distance. Typically the probe distance is maintained by means of a mechanical link whose length is adjustable. Therefore it is important to have a measurement method which can confirm that the length of adjustable link has not been inadvertently changed, and that the defined probe distance is effectively maintained throughout a lengthy series of inspections.

There therefore exists a need for a method of accurately determining the acoustic velocity in the test object during the inspection so that the TFM images resulting from the inspection will provide a reliable measure of the intensity of indications.

Furthermore, there also exists a need for a method of accurately determining the distance between probes during a P-C FMC-TFM inspection.

SUMMARY OF THE INVENTION

Accordingly, it is a general objective of the present disclosure to provide a real-time method of accurately determining the acoustic velocity in the test object.

It is further an objective of the present disclosure to provide a real-time method of determining the acoustic velocity which does not require presence of a flaw in the test object.

It is further an objective of the present disclosure to provide a real-time method of determining the velocities of both the S-wave and the P-wave in the test object.

It is further an objective of the present disclosure to provide a real-time method of determining the acoustic velocities in a steel test object either in the presence or absence of a weld cap.

It is further an objective of the present disclosure to provide a real-time method of determining the separation distance between two probes in a P-C FMC-TFM acquisition.

These objectives are achieved in the present disclosure by determining the times-of-flight of both the P-type surface wave and the Rayleigh surface wave generated at the critical angles between the wedge and the test object. Since the wedge properties are known, if the time-of-flight is determined, the associated acoustic velocity in the test object may also be determined. Knowing the acoustic velocities of P-waves and Rayleigh waves, the velocity of S-waves in the test object may be calculated. In addition, with knowledge of the acoustic velocities, the probe separation may be determined by time-of-flight measurements.

DETAILED DESCRIPTION OF PREFERRED EMBODIMENT

Symbol Definitions

Figure 2:
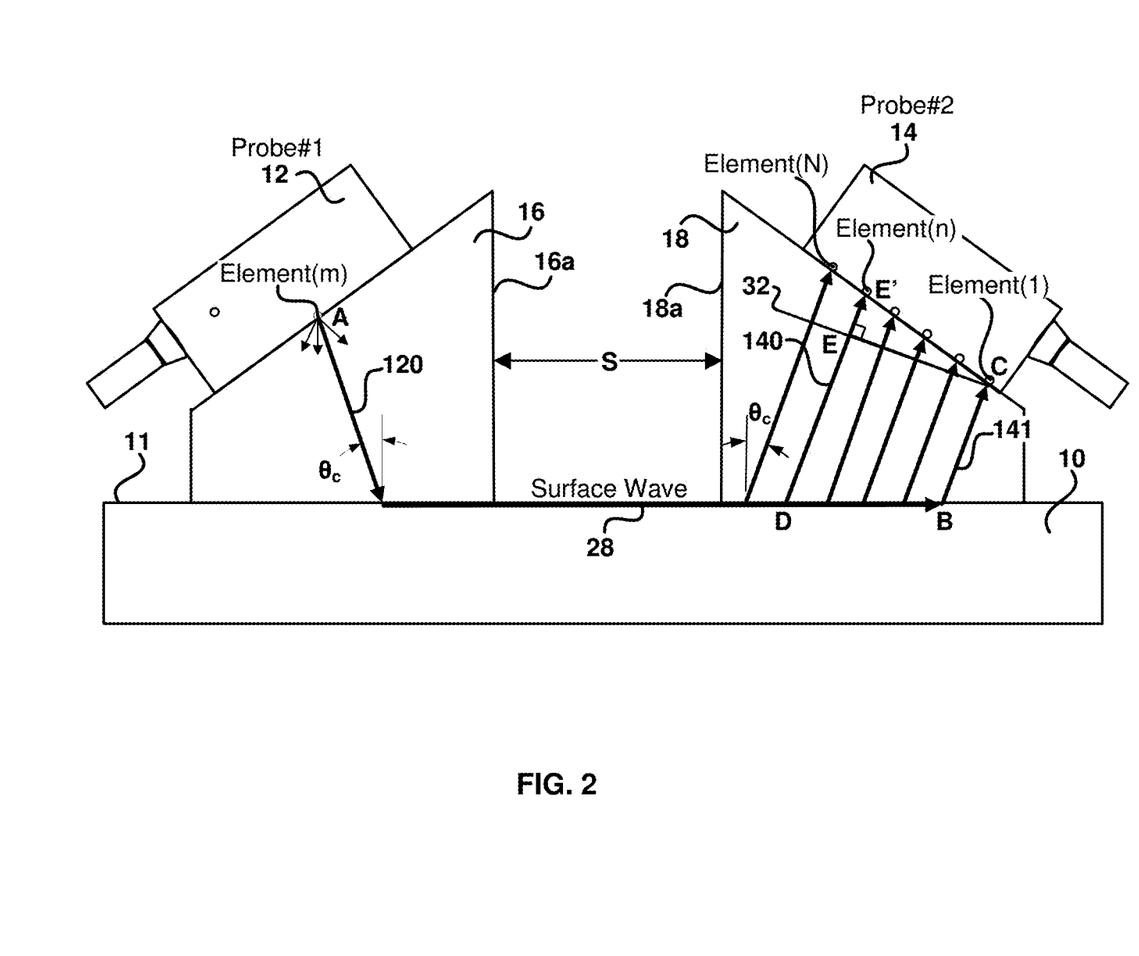
FIG. 2 is a schematic of setup geometry according to the present disclosure, showing emitted and received acoustic beams at the critical angle.

M number of emitting elements
N number of receiving elements
$\theta_C$ critical angle
$\theta_P$, $\theta_R$ critical angles for P-waves, Rayleigh waves
V acoustic velocity
$V_P$, $V_R$, $V_S$ acoustic velocities for P-waves, Rayleigh waves, S-waves
$V_W$ acoustic velocity in receiving wedge
S probe separation
$\tau$ constant time-of flight
$\tau_P$, $\tau_R$ constant times-of flight for P-waves, Rayleigh waves
$\tau_0$ reference constant time-of flight for S=0
$\delta t_n$ reception delay of $n^{th}$ receiving element
$\alpha$ angular offset of received wavefront
$t_{An}$ time-of-flight from emitting element to $n^{th}$ receiving element
$d_n$ distance from $1^{st}$ to $n^{th}$ receiving element
p pitch of receiving elements FIG. 2 shows an embodiment of the setup geometry for performing measurements according to the present disclosure. A first phased array probe 12 and a second phased array probe 14 are acoustically coupled to a first wedge 16 and a second wedge 18 respectively. Wedges 16 and 18 are in contact with a surface 11 of a test object 10, and in a preferred embodiment are located on either side of a weld in test object 10 (not shown) which is to be inspected.

For the purposes of the present disclosure, the following assumptions are made:
 i. The wedge angles of wedges 16 and 18 are accurately known.
 ii. The acoustic velocity of P-waves in wedges 16 and 18 is accurately known.
 iii. Surface 11 of test object 10 is flat, except for the optional presence of a weld cap between wedges 16 and 18.
 iv. All the active elements of probes 12 and 14 are located in the same plane.
 v. The probes operate in "pitch-catch" mode during FMC acquisition, meaning that echo signals from acoustic pulses emitted by an active element on one probe are only received by active elements on the other probe.

As shown in FIG. 2, wedge 16 and wedge 18 are separated by a distance S which is measured between a surface 16a of wedge 16 and a surface 18a of wedge 18, wherein surfaces 16a and 18a are substantially perpendicular to surface 11 of test object 10. It is further assumed that probe 12 comprises M emitting elements designated element (m) for m=1 to M, and that probe 14 comprises N receiving elements designated element (n) for n=1 to N.

FIG. 2 illustrates a representative element (m) located at a point A of probe 12, and emitting ultrasonic beams in multiple directions, including an ultrasonic beam 120 which intersects surface 11 at the critical angle $\theta_c$ for the interface between wedge 16 and test object 10. Since beam 120 is at the critical angle, a surface wave 28 is generated at the interface and propagates within test object 10 just below surface 11. Surface wave 28 propagates to the interface between surface 11 and wedge 18, where the acoustic energy may enter wedge 18 as a plurality of ultrasonic beams having a wavefront 32 at the critical angle $\theta_c$, which may be received by all N elements of probe 14. FIG. 2 illustrates a plurality of beams being received by probe 14, including a beam 140 which emanates from a point D on surface 11 and is received by a representative element (n) located at a point E' on probe 14, and a beam 141 which emanates from a point B on surface 11 and is received by element (1), the first element in the array of probe 14, which is located at a point C on probe 14. Note that, since wedges 16 and 18 are made of the same material, the critical angle between wedge 16 and surface 11 is the same as the critical angle between wedge 18 and surface 11.

As shown in FIG. 2, beam 140 intersects wavefront 32 at a point E. Note however, that a reception delay may be applied to element (n) so that the virtual position of element (n) is at point E on wavefront 32. Similarly, appropriate delays may be applied to all elements of probe 14 so that the virtual positions of all receiving elements are on wavefront 32.

It should also be noted that surface wave 28 comprises a mixture of P-waves and Rayleigh waves, wherein the P-waves are P-polarized (vibrations parallel to the propagation direction) and the Rayleigh waves are a mixture of P- and S-polarizations (elliptical vibrations). The P-waves propagating in surface wave 28, also known as lateral waves, have the same velocity as bulk P-waves propagating in the volume of test object 10. In the present disclosure, use of the term "P-wave" will include both surface P-waves and bulk P-waves.

Figure 3:
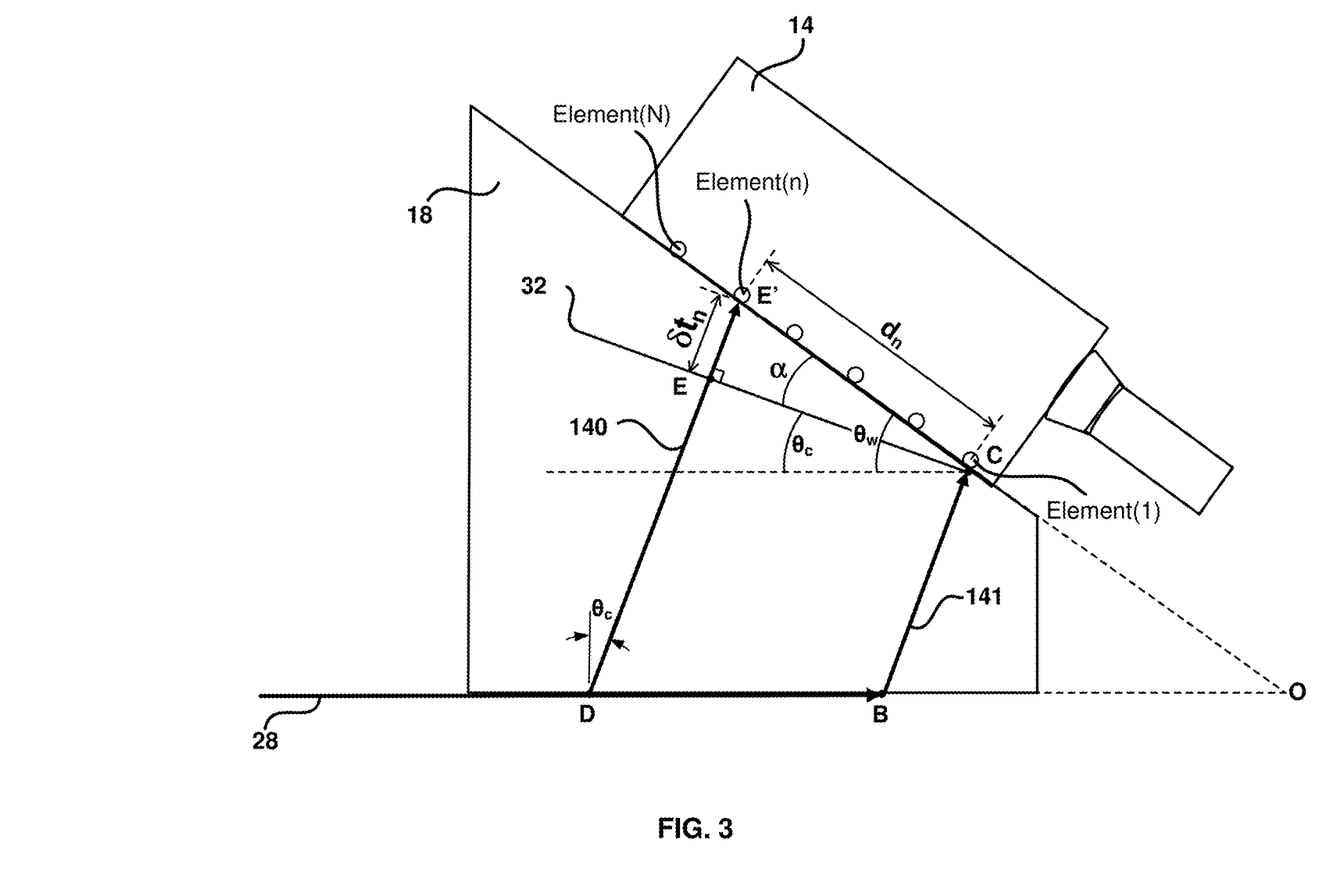
FIG. 3 is an expanded view of the geometry of the receiving probe according to the present disclosure.

Note that the critical angle for a P-wave is different from the critical angle for a Rayleigh wave and therefore critical angle $\theta_c$ as shown in FIGS. 2 and 3 should be interpreted as having two values, namely $\theta_{c,P}$ for the P-waves and $\theta_{c,R}$ for the Rayleigh waves. The P-waves have an acoustic velocity $v_P$, and the Rayleigh waves have an acoustic velocity $v_R$ which is known to be linked to the velocities of both P- and S-waves in test object 10 according to the following equation, which is well-known in the art (see for example, Jr. Lester W. Schmerr, *Fundamentals of Ultrasonic Nondestructive Evaluation—A Modeling Approach*, Plenum Press, 1998):

$$\left(2 - \frac{v_R^2}{v_S^2}\right)^2 - 4 * \left(1 - \frac{v_R^2}{v_P^2}\right)^{\frac{1}{2}} * \left(1 - \frac{v_R^2}{v_S^2}\right)^{\frac{1}{2}} = 0 \quad (1)$$

where $v_S$ is the S-wave wave velocity in test object 10.

Hereinafter, the acoustic velocity of surface wave 28 in test object 10 will be designated v, where it is understood that $v=v_P$ for P-waves and $v=v_R$ for Rayleigh waves.

Still referring to FIG. 2, it is important to note that the inventors of the present disclosure have discovered that the times-of-flight from transmitting element (m) at point A on probe 12 to a point on wavefront 32 corresponding to any of the receiving elements on probe 14 are all equal to each other when beam 120 is at the critical angle $\theta_c$. This concept may be generalized to state that, if a set of appropriate delays is applied to receiving elements (n) so that the equivalent reception time of each element (n) corresponds to reception at wavefront 32, then the times-of-flight from transmitting element (m) on probe 12 to receiving element (n) on probe 14 are the same for all values of m and n when emitting and receiving beams are at their corresponding critical angle.

Hence, one of the novel and important aspects of the present disclosure is application to the determination of acoustic velocities in the test object of the above explained newly discovered concept of equal times-of-flight when the emitted and received beams are at the critical angle Another novel and important aspect of the present disclosure is application of the above explained concept of equal times-of-flight together with the operation of "pitch-catch" mode and FMC acquisition to derive the P-wave and shear-wave velocities during an inspection operation. Determination of acoustic velocities in the actual test object during the inspection has many significant benefits. For example, complicated processes of determining sound velocity in a calibration block in existing practice are avoided. Accuracy of the inspection does not have to be compromised by using an assumed acoustic velocity, or by measuring acoustic velocity in a material which does not correspond exactly to the test object.

FIG. 3 shows an expanded view of wedge 18 and probe 14, showing only beams 140 and 141 which are received by representative element (n) and first element (1) respectively. Applying Snell's law to surface wave 28 propagating at 90° angle:

$$v = \frac{v_w}{\sin \theta_c} \quad (2)$$

where $v_w$ is the velocity of P-waves in the wedge, which is known because the properties of the wedge material are known and produced with known tolerances. In equation (2) it is understood that v and $\theta_c$ may take values for either P- or Rayleigh surface waves.

Still referring to FIG. 3, it is seen that:

$$t_{DE} = \frac{DE}{v_w} \quad (3)$$

$$t_{DBC} = \frac{DB}{v} + \frac{BC}{v_w} \quad (4)$$

where $t_{DE}$ is the time-of-flight for waves propagating between points D and E, and $t_{DBC}$ is the time-of-flight for waves propagating between points D, B and C. By applying Snell's law (equation (2)) and the geometry of similar triangles OBC and ODE, it can be shown that when beams 140 and 141 are at the critical angle $\theta_c$ $$t_{DE} = t_{DBC} \quad (5)$$

Since beam 140 and element (n) are representative of all beams received by all elements of probe 14, equation (5) shows that the time-of-flight is the same for all elements of probe 14. Therefore:

$$t_{An} = \tau \quad (6)$$

where $t_{An}$ is the time-of-flight from point A to receiving element (n) and $\tau$ is a constant value of time-of-flight. Note that the constant time-of-flight $\tau$ has a value $\tau_P$ for P-waves and a value $\tau_R$ for Rayleigh waves.

A preferred method of data acquisition according to the present invention is to fire any element (m) of probe 12 and to acquire A-scans for all N elements of probe 14. In this case, probe 12 is the emitting probe, wedge 16 is the emitting wedge, probe 14 is the receiving probe and wedge 18 is the receiving wedge. By the principle of reversibility, an alternative method is to fire any element (n) of probe 14 and to acquire A-scans for all M elements of probe 12. In this case, probe 14 is the emitting probe, wedge 18 is the emitting wedge, probe 12 is the receiving probe and wedge 16 is the receiving wedge.

It will be shown below that the acquired A-scan data may be used to determine $v_P$, $v_R$, $v_S$ and probe separation S.

Still referring to FIG. 3, element (n) at point E' has an applied reception delay of $\delta t_n$ which produces an angular offset $\alpha$ of wavefront 32 relative to the surface of wedge 18. At the critical angle for surface wave 28:

$$\theta_c = \theta_w - \alpha \quad (7)$$

where $\theta_w$ is the wedge angle of wedge 18. The applied delay $\delta t_n$ is given by:

$$\delta t_n = \frac{d_n * \sin \alpha}{v_w} \quad (8)$$

where $d_n$ is the distance CE' between element (1) and element (n).

By inserting equations (2) and (7) into equation (8), the following equation is obtained:

$$\delta t_n = \frac{d_n}{v_w} * \left( \sin \theta_w * \sqrt{1 - \left(\frac{v_w}{v}\right)^2} - \left(\frac{v_w}{v}\right) * \cos \theta_w \right) \quad (9)$$

Equation (9) expresses the applied delay $\delta t_n$ for an element (n) at position $d_n$ as a function of the surface wave velocity v and known wedge properties $v_w$ and $\theta_w$. According to the method of the present disclosure, a set of reception delays $\delta t_n$ is determined so that equation (6) is satisfied, meaning that the time-of-flight $t_{An}$ is constant and angular offset $\alpha$ corresponds to reception at critical angle $\theta_c$. Equation (9) may then be used to determine surface wave velocity v.

Note that for the particular case of wedge 18 being a flat wedge, where $\theta_w = 0$, equation (9) reduces to:

$$\delta t_n = -\frac{d_n}{v} \quad (10)$$

so that the measurement of the surface wave velocity v is independent of the wedge velocity $v_w$. The negative sign in equation (10) indicates that element (1) is delayed with respect to element (n), unlike the case illustrated in FIG. 3 where element (n) is delayed with respect to element (1).

Note that, although in FIGS. 2 and 3 wedges 16 and 18 are depicted as having the same wedge angle, this is not a requirement for the invention. Wedge 16 may have a wedge angle $\theta_w'$ which is different from the wedge angle $\theta_w$ of wedge 18. Note that although the wedge angles may be different, critical angle $\theta_c$ will be the same at the interface between wedge 16 and surface 11 as at the interface between wedge 18 and surface 11, provided that wedges 16 and 18 are made of the same material. Also note that, when wedge angles of wedges 16 and 18 are not equal, delays $\delta t_n$ required to satisfy equation (6) will be different when probe 14 is the emitting probe and wedge 18 is the emitting wedge, from the delays required when probe 12 is the emitting probe and wedge 16 is the emitting wedge.

Figure 4:
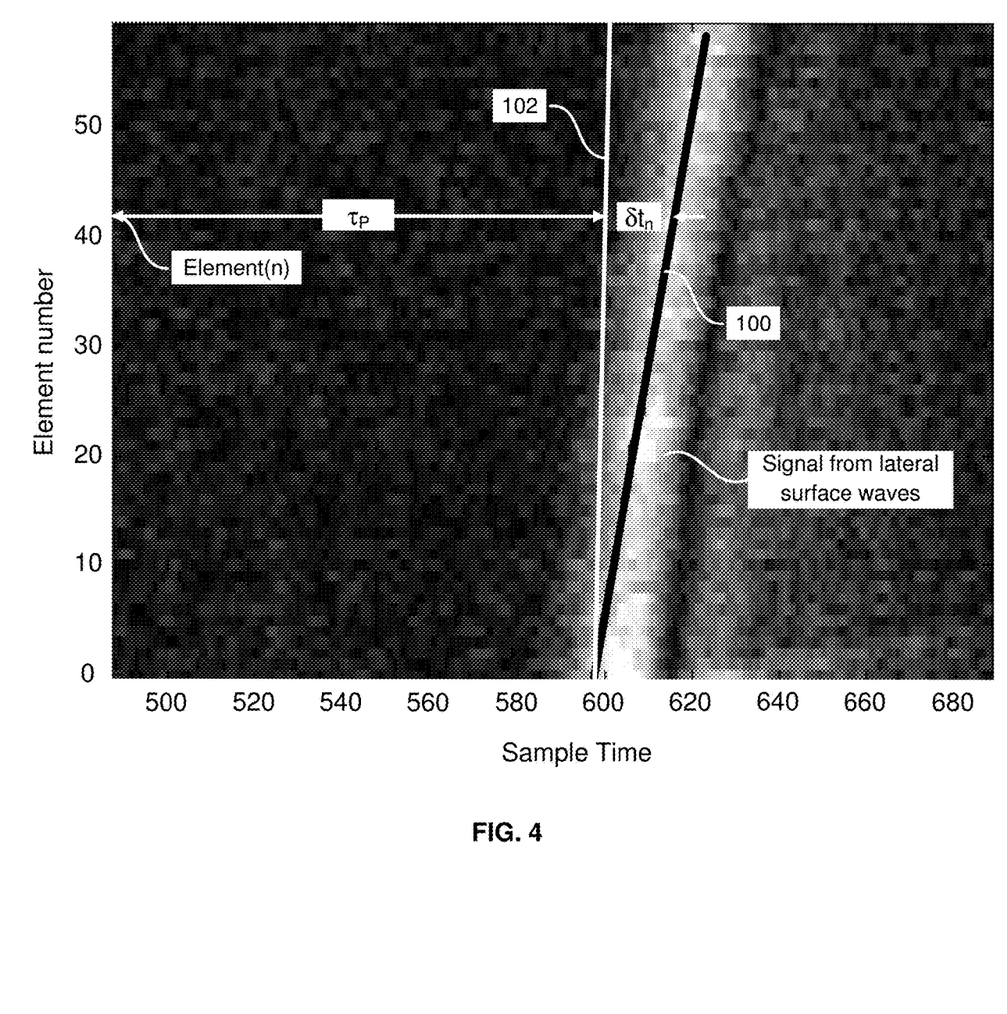
FIG. 4 is a plot of surface P-wave A-scan signals from each element of the receiving probe.

FIG. 4 is an plot representing A-scans of P-surface waves generated by firing of a single element (m) of probe 12 and received by an embodiment of probe 14 having 60 receiving elements. Note that, in the plot of FIG. 4, no reception delays have been applied to the elements of probe 14. Because surface waves are the only waves able to take a direct path without reflections from probe 12 to probe 14, and because the P-surface waves have the highest acoustic velocity, the first signals to be acquired by probe 14 are the P-surface waves. These earliest A-scan signals may be identified as P-wave regions of interest in A-scans from all the elements of probe 14, and it is these signals which are displayed in FIG. 4. The Rayleigh surface waves will reach probe 14 at a later time than the P-waves, and since the velocity ratio between P- and Rayleigh waves is approximately known and the travel time in wedge 18 is known, the arrival time of the Rayleigh waves at probe 14 may be approximately defined. Therefore Rayleigh wave regions of interest may be identified in A-scans from all the elements of probe 14, and a plot representing A-scans of Rayleigh surface waves (not shown) may be constructed in a manner analogous to the construction of FIG. 4.

Continuing to refer to FIG. 4, a line 100 is a linear best fit to the maximum values of the P-wave signals in the A-scans from all elements of probe 14. However, if equation (6) is valid so that the time-of-flight from element (m) of probe 12 to any receiving element (n) of probe 14 is constant, then line 100 should be vertical. The deviation of line 100 from a vertical line 102 therefore represents the best fit for the receiving delay $\delta t_n$ to be applied to each element (n) in order to cause line 100 to coincide with line 102, thereby satisfying equation (6), wherein there is a constant time-of-flight $\tau_P$ to all elements (n). Note that, since the elements of probe 14 are distributed with constant pitch, the delays applied are a linear function of n, so that:

$$\delta t_n = \varepsilon * n \quad (11)$$

Noting that $d_n - d_{n-1} = p$, and inserting equation (11) into equation (9):

$$\varepsilon = \frac{p}{v_w} * \left( \sin \theta_w * \sqrt{1 - \left(\frac{v_w}{v}\right)^2} - \left(\frac{v_w}{v}\right) * \cos \theta_w \right) \quad (12)$$

where p is the pitch of the elements of probe 14, and $v = v_P$ for P-waves or $v = v_R$ for Rayleigh waves.

Use of equation (12), together with the slope of delays determined from FIG. 4, enables the P-wave velocity $v_P$ in test object 10 to be calculated. Similarly, using equation (12) together with the slope of delays determined from a plot for Rayleigh waves analogous to FIG. 4, enables $v_R$, the velocity of Rayleigh waves, to be calculated.

Having determined $v_P$ and $v_R$, the S-wave velocity $v_S$ in test object 10 may be calculated from equation (1).

Once the surface P-wave velocity $v_P$ and the appropriate reception delays $\delta t_n$ are known, the distance S between probes 12 and 14 may be determined by time-of-flight measurements. A reference acquisition with a single emitting element (m) on probe 12 is first performed with wedges 16 and 18 both in contact with test object 10, but with surfaces 16a and 18a of the respective wedges in contact so that separation distance S=0. The reference acquisition enables measurement of a reference propagation delay $\tau_0$ from emitting element (m) on probe 12 to any receiving element (n) on probe 14. Optionally, in order to validate that the wedge parameters are correct and applicable to both wedge 12 and wedge 14, a second reference acquisition may be performed with a single emitting element (n) on probe 14, measuring reference propagation delay $\tau_0'$ from emitting element (n) on probe 14 to any receiving element (m) on probe 12. If wedge parameters are valid, measurements of $\tau_0$ and $\tau_0'$ should be in close agreement, and an average value may be used in equation (13) below.

Wedges 16 and 18 are then moved apart by distance S and acquisition measurements are repeated, measuring propagation delay $t_{An}$ from a single emitting element (m) on probe 12 to any receiving element (n) on probe 14, and optionally a propagation delay $t_{An}'$ from a single emitting element (n) on probe 14 to any receiving element (m) on probe 12. If wedge parameters are valid, measurements of $t_{An}$ and $t_{An}'$ should be in close agreement, and an average value may be used to derive the constant time-of-flight value $\tau_P$ in equation (6) applied to P-waves. The separation S may then be determined from the following equation:

$$S = v_P * (\tau_P - \tau_0) \quad (13)$$

Note that equation (13) assumes that $v_p$ does not change significantly in the time between measurements of $\tau_P$ and $\tau_0$.

Note that an alternative method of data acquisition according to the present disclosure is to sequentially fire multiple emitting elements (m) in probe 12. Noting that critical angle $\theta_c$ must be the same irrespective of the emitting element (m), and acquiring data at all elements (n) for transmissions at each of elements (m), receiving delay $\delta t_n$ may be determined for each of the emitting elements (m) in a manner analogous to the method described above in connection with FIG. 4. Equations (12) and (13) may then be used to derive independent measurements of $v_P$, $v_R$ and S for each of the emitting elements (m). Use of multiple emitting elements (m) may result in more accurate measurements and more sensitive validation of the accuracy of setup parameters of the inspection. All such use of multiple emitting elements is within the scope of the present disclosure.

Figure 5:
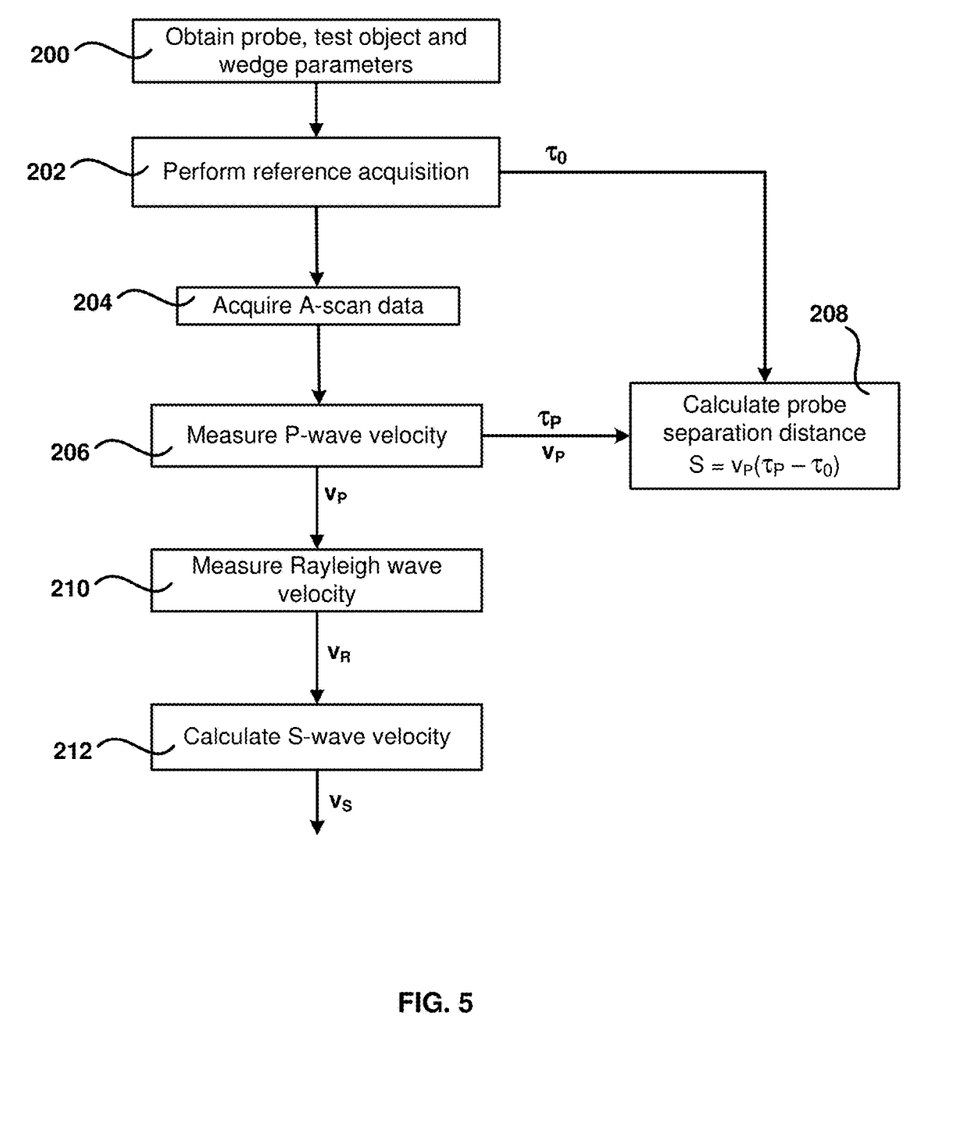
FIG. 5 is a schematic of an inspection method according to the present disclosure.

FIG. 5 is a schematic of an inspection method according to the present disclosure. In step 200, parameters of the probe, test object and wedges necessary for the inspection are obtained. These parameters include the number of elements N, the pitch p, the wedge angle $\theta_w$, the wedge velocity $v_w$, and the material of test object 10 (allowing the Rayleigh wave region of interest to be estimated). In step 202, a reference acquisition is performed to determine reference propagation delay $\tau_0$. In step 204, A-scan data is acquired by firing any one of the elements of probe 12 and recording corresponding A-scans from each of the receiving elements of probe 14. In step 206 the velocity of the P-type surface wave, $v_P$, is measured by adjusting reception delays of probe 14 so that time-of-flight $t_{An}$ is a constant time-of-flight $\tau_P$. In step 208, the values of $v_P$ and $\tau_P$ determined in step 206, as well as the value of $\tau_0$ determined in step 202, are used to calculate probe separation S by means of equation (13). In step 210, the velocity of the Rayleigh surface wave, $v_R$, is measured in analogous fashion to measurement of $v_P$ in step 206. In step 212, values of $v_P$ and $v_R$ are used in equation (1) to calculate the S-wave velocity $v_S$ in test object 10.

Figure 6A:
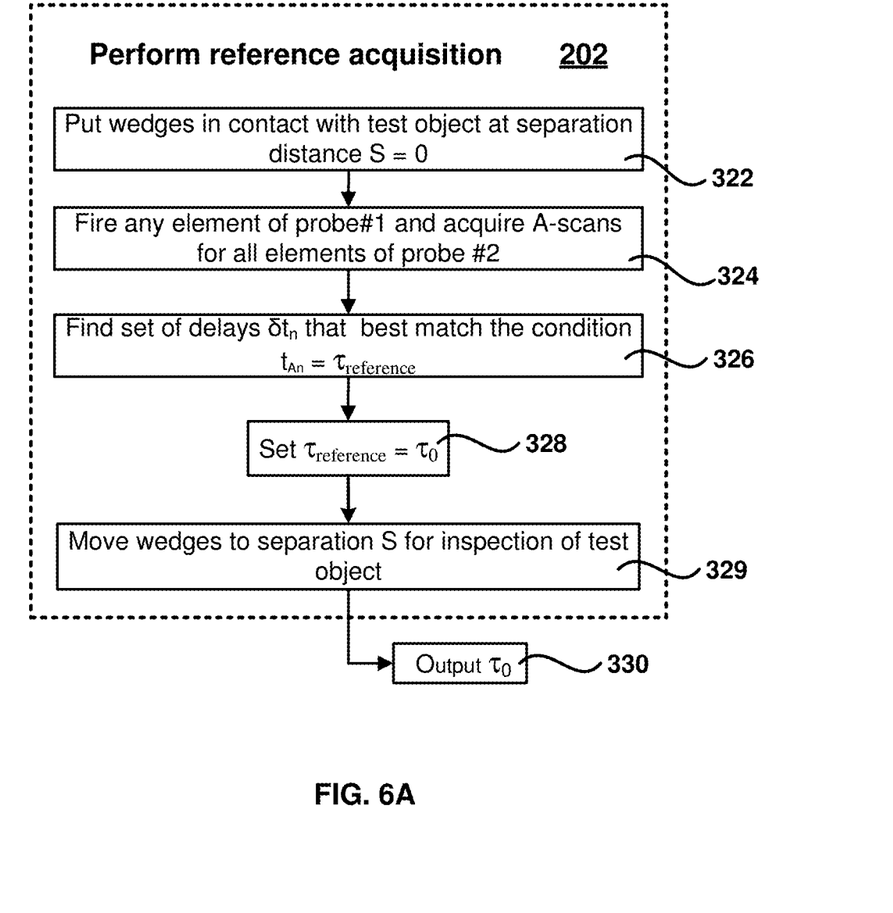
FIG. 6A is a schematic of a reference acquisition method according to the present disclosure.

Step 202, the step of performing a reference acquisition, further comprises the steps shown in FIG. 6A. In step 322, wedges 16 and 18 are put in contact with test object 10 at a separation distance S=0. In step 324, any one element of probe 12 is fired and corresponding A-scans from each of the receiving elements of probe 14 are recorded. Optionally, step 324 may also include firing any element of probe 14 and recording corresponding A-scans from each of the receiving elements of probe 12. In step 326, a set of delays $\delta t_{n|reference}$ is found that best matches the condition $t_{An}=\tau_{reference}$, meaning that the arrival time of the P-waves from probe 12 is the same at all elements of probe 14 for the reference condition of S=0. In step 328, reference propagation delay $\tau_0$ is set equal to the average value of the constant $\tau_{reference}$. In step 329, wedges 16 and 18 are moved to separation S in locations convenient for inspection of test object 10. For example, if a weld in test object 10 is being inspected, wedges 16 and 18 may be moved to locations on either side of the weld. In step 330, the value of $\tau_0$ is output for use step 208, calculating probe separation distance (see FIG. 5).

Figure 6B:
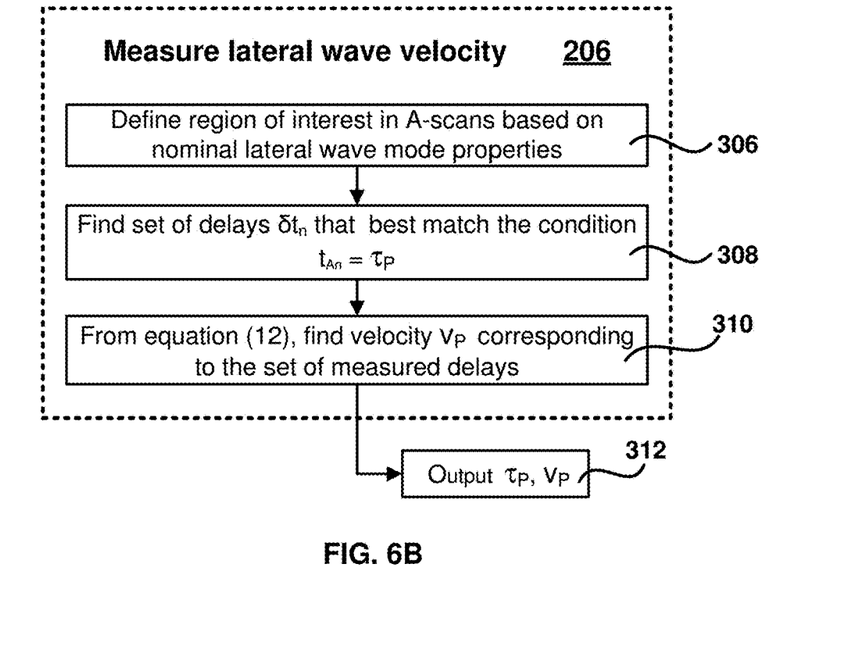
FIG. 6B is a schematic of a method of measuring P-wave velocity according to the present disclosure.

Step 206, the step of measuring the P-wave velocity, further comprises the steps shown in FIG. 6B. In step 306, a region of interest is defined for each of the A-scans acquired in step 204 (see FIG. 5), the region of interest being defined based on nominal P-wave properties. In an embodiment, the nominal P-wave property is that the P-surface waves have the highest acoustic velocity, and are therefore the earliest signals in the A-scans acquired by probe 14. In step 308, a set of delays $\delta t_{n|p}$ is found that best matches the condition $t_{An}=\tau_P$, meaning that the arrival time of the P-waves is the same at all elements of probe 14. In step 310, equation (12) is used to find the velocity $v_P$ corresponding to the set of delays $\delta t_n$, and in step 312 the values of $\tau_P$ and $v_P$ are output.

Figure 6C:
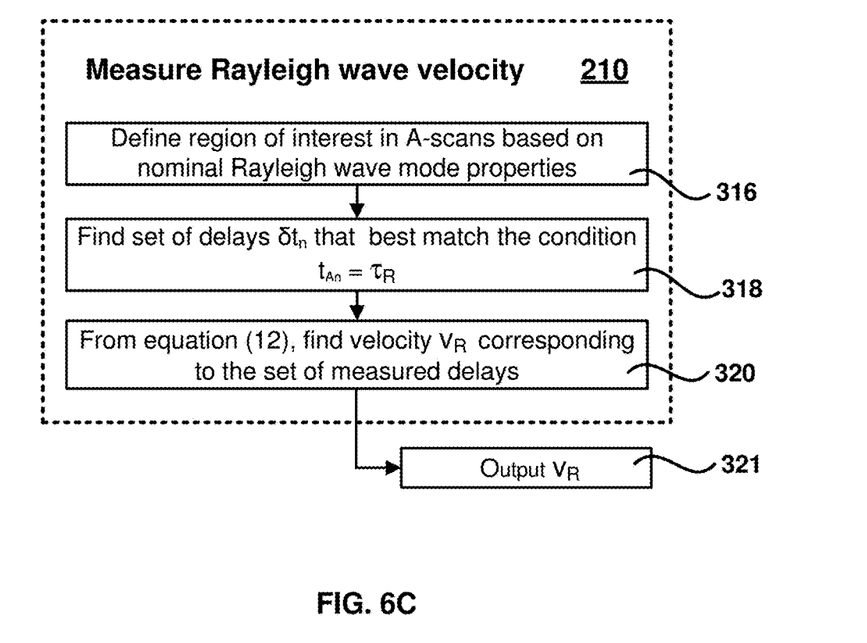
FIG. 6C is a schematic of a method of measuring Rayleigh wave velocity according to the present disclosure.

Step 210, the step of measuring the Rayleigh velocity, further comprises the steps shown in FIG. 6C. In step 316, a region of interest is defined for each of the A-scans acquired in step 204 (see FIG. 5), the region of interest being defined based on nominal Rayleigh wave properties. In an embodiment, the nominal Rayleigh wave properties are that:
  i. the Rayleigh surface waves, having lower acoustic velocity will reach probe 14 at a later time than the P-waves, and
  ii. the velocity ratio between P- and Rayleigh waves is approximately known and the travel time in wedge 18 is known, and therefore the arrival time of the Rayleigh waves at probe 14 may be approximately known, enabling a region of interest to be defined.

In step 318, a set of delays $\delta t_{n|R}$ is found that best matches the condition $t_{An}=\tau_R$, meaning that the arrival time of the Rayleigh waves is the same at all elements of probe 14. In step 320, equation (12) is used to find the velocity $v_R$ corresponding to the set of delays $\delta t_n$, and in step 321 the value of $v_R$ is output.

Figure 7A:
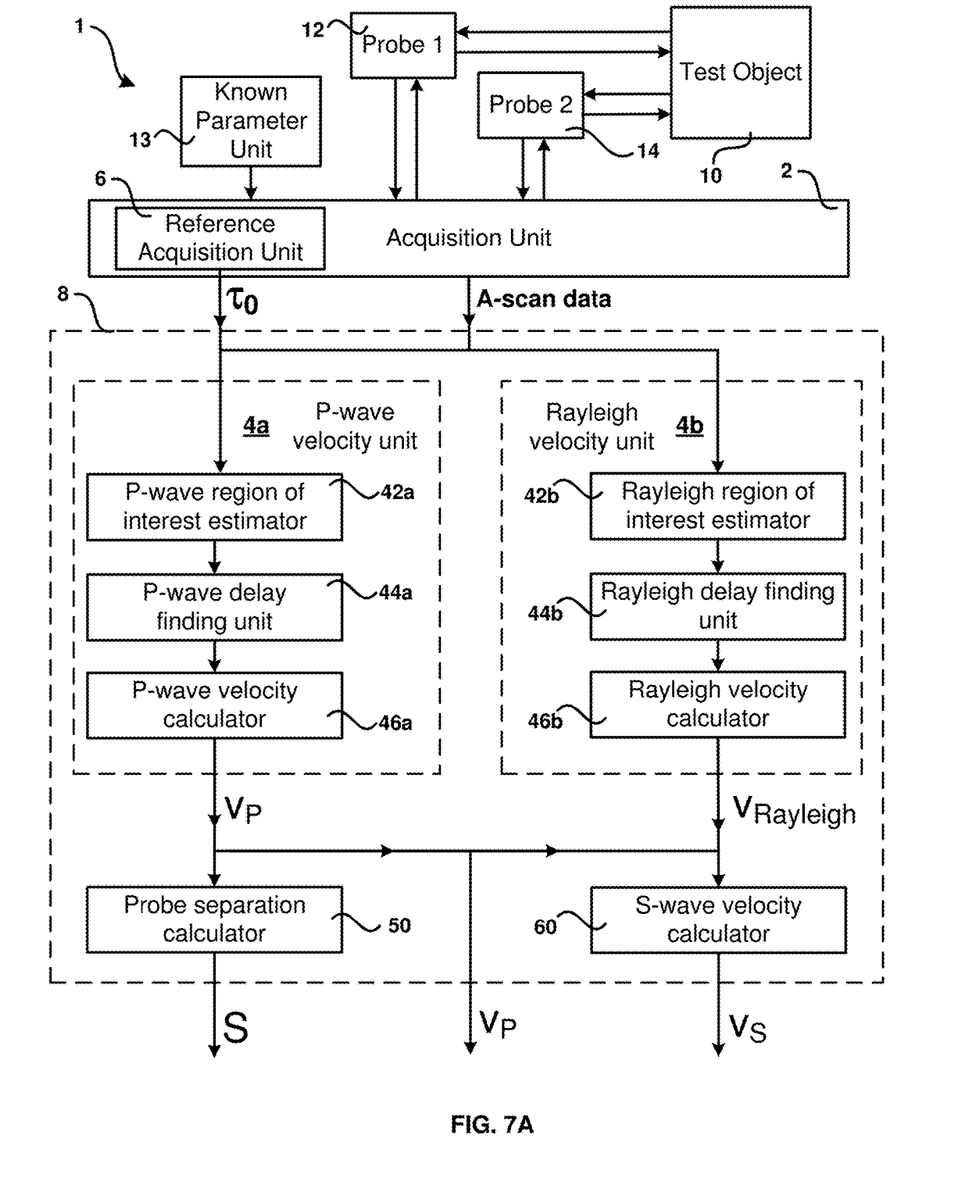
FIG. 7A is a schematic of a surface wave time-of-flight system for determining acoustic velocities and probe separation according to the present disclosure.

FIG. 7A is a schematic representation of a probe separation and velocity measurement system 1 for determining acoustic velocities and probe separation according to the present disclosure. Data from probes 12 and 14 in acoustic contact with test object 10 are acquired and digitized by an acquisition unit 2. Acquisition unit 2 acquires known parameters from a known parameter unit 13 and transfers A-scan data to a computer processor 8. Acquisition unit 2 includes a reference acquisition unit 6 which transfers reference propagation delay $\tau_0$ to computer processor 8. Computer processor 8 comprises a P-wave velocity unit 4a, a Rayleigh velocity unit 4b, a probe separation calculator 50 and a S-wave velocity calculator 60.

The known parameters in known parameter unit 13 comprise the number N of the receiving elements of the receiving probe, the pitch p, the wedge angle $\theta_w'$ of wedge 16, the wedge angle $\theta_w$ of receiving wedge 18, and the wedge velocity $V_w$.

P-wave velocity unit 4a comprises a P-wave region of interest estimator 42a for estimating regions of interest for P-waves in the A-scans, a P-wave delay finding unit 44a for finding a set of delays $\delta t_{n|P}$ that best matches the condition $t_{An}=\tau_P$ for P-waves, and a P-wave velocity calculator 46a for calculating the P-wave velocity in test object 10 based on equation (12) and the measured delays. Output from P-wave velocity unit 4a is $v_P$, the P-wave velocity in test object 10.

Rayleigh velocity unit 4b comprises a Rayleigh region of interest estimator 42b for estimating regions of interest for Rayleigh waves in the A-scans, a Rayleigh delay finding unit 44b for finding a set of delays $\delta t_{n|R}$ that best matches the condition $t_{An}=\tau_R$ for Rayleigh waves, and a Rayleigh velocity calculator 46b for calculating the Rayleigh velocity in test object 10 based on equation (12) and the measured delays. Output from Rayleigh velocity unit 4b is $v_R$, the Rayleigh velocity in test object 10.

S-wave velocity calculator 60 receives input of $v_P$ from P-wave velocity unit 4a and $v_R$ from Rayleigh velocity unit 4b, and using equation (1) calculates $v_S$, the S-wave velocity in test object 10.

Probe separation calculator 50 receives input of $v_P$ and $\tau_P$ from P-wave velocity unit 4a, and reference propagation delay $\tau_0$ from reference acquisition unit 6, and using equation (13) calculates probe separation S between wedges 16 and 18.

Figure 7B:
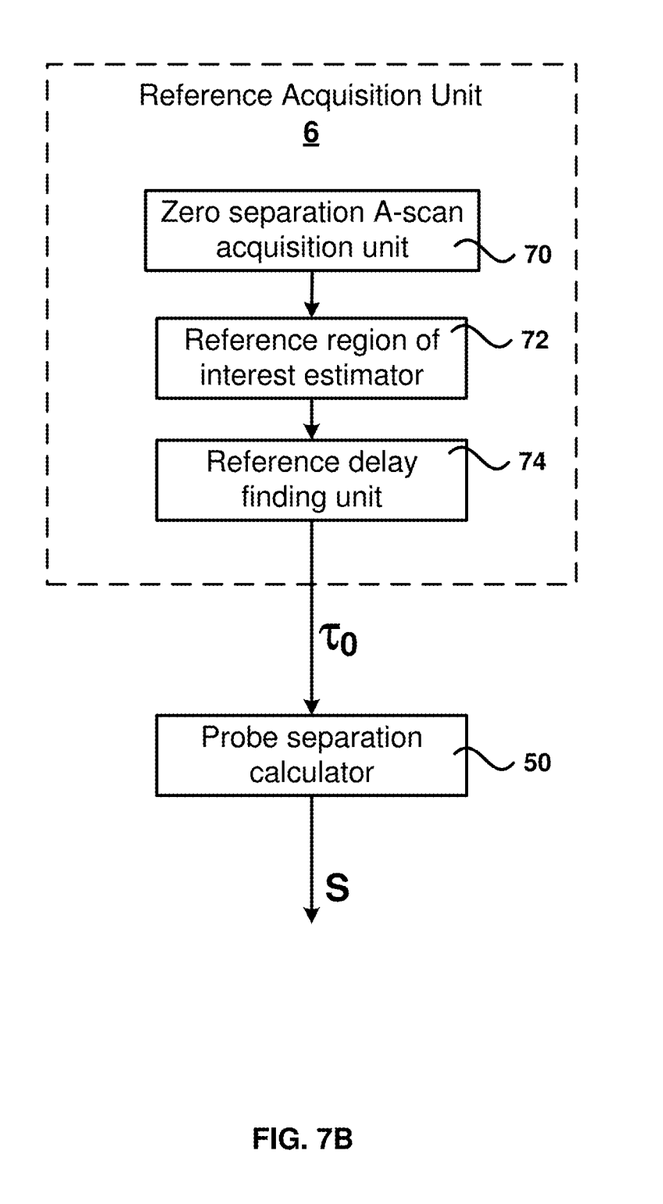
FIG. 7B is a schematic of a reference acquisition unit according to the present disclosure.

As shown in FIG. 7B, reference acquisition unit 6 further comprises a zero separation A-scan acquisition unit 70, a reference region of interest estimator 72 and a reference delay finding unit 74. Reference acquisition unit 6, zero separation A-scan acquisition unit 70, reference region of interest estimator 72 and reference delay finding unit 74 operate only when there is zero separation distance between wedge 16 and wedge 18, namely when surface 16a of wedge 16 is in contact with surface 18a of wedge 18.

Zero separation A-scan acquisition unit 70 is configured to fire a selected element of probe 12 and to acquire A-scans from each element (n) of probe 14. Reference region of interest estimator 72 is configured to estimate regions of interest for P-waves in the A-scans, and reference delay finding unit 74 is configured to find a set of delays $\delta t_{n|reference}$ that best matches the condition that time-of-flight $t_{An}=\tau_{reference}$ for P-waves at zero separation, where $\tau_{reference}$ is a constant equal to $\tau_0$, the reference propagation delay. The reference propagation delay to is output from reference acquisition unit 6 to probe separation calculator 50. Probe separation calculator 50 operates when probe separation is non-zero, and calculates the value of probe separation S according to equation (13).

Note that the outputs of probe separation and velocity measurement system 1 are the acoustic velocities in test object 10 necessary for TFM time-of-flight calculations using FMC data. These velocity values pertain to the actual material condition of test object 10 and therefore provide more accurate and reliable TFM imaging than prior art methods in which velocity is measured in a calibration block, rather than in test object 10 itself. Probe separation and velocity measurement system 1 also provides an actual measurement of probe separation for the FMC acquisition, probe separation being another sensitive determining factor for time-of-flight calculations.

It should be noted that use of pitch-catch mode with two probes is an embodiment of the invention, but that other embodiments including use of a single probe comprising both emitting and receiving elements are also within the scope of the present disclosure.

Note also that, although the method of FIG. 5 and the system of FIG. 7A are illustrated as encompassing determination of $v_P$, $v_R$, $v_S$, and S, there is utility in a method or system configured to determine only $v_P$. For example, for a TFM image using only P-waves, knowledge of only $v_P$ may be required. Such a determination of only $v_P$ may be achieved using a single array probe on a zero degree (flat) wedge, where the probe comprises both transmitting and receiving elements. After measuring the receiving delay $\delta t_n$, P-wave velocity $v_P$ may be determined by applying equation (10). Other methods of determining only $v_P$ may be devised from the present teaching, and all such methods are within the scope of the present disclosure.

Although the present invention has been described in relation to particular embodiments thereof, it can be appreciated that various designs can be conceived based on the teachings of the present disclosure, and all are within the scope of the present disclosure.

What is claimed is:

1. A method of determining ultrasonic velocity in a test object using an ultrasonic measurement system, the system having an emitting probe operable with an emitting wedge and a receiving probe operable with a receiving wedge, the wedges configured to be in contact with a test surface of the test object, wherein the receiving probe is an array probe having a number N of receiving elements, the receiving elements designated element (n) for n=1 to N, the method comprising the steps of:
   obtaining known parameters for the probes and the wedges;
   firing at least one emitting element of the emitting probe, thereby causing the at least one emitting element to emit beams of ultrasonic energy into the emitting wedge, including a critical beam at a critical angle which generates a surface wave of ultrasonic energy propagating near the test surface in the test object towards the receiving wedge;
   receiving corresponding A-scans from each element (n) of the receiving probe, the A-scans comprising amplitudes of received echo signals as a function of arrival times at each element (n); and,
   determining at least one surface wave velocity of the surface wave, and,
   wherein the known parameters comprise the number N of the receiving elements, a pitch p, wherein p is the distance between adjacent receiving elements, an emitting wedge angle $\theta_w{'}$ of the emitting wedge, a receiving wedge angle $\theta_w$ of the receiving wedge, and a wedge velocity $V_w$, wherein $V_w$ is the velocity of longitudinal waves in the receiving wedge.

2. The method of claim 1 wherein the at least one surface wave velocity is a longitudinal wave (P-wave) velocity $V_P$ of a P-type surface wave.

3. The method of claim 1 wherein the at least one surface wave velocity is a longitudinal wave (P-wave) velocity $V_P$ of a P-type surface wave and a Rayleigh wave velocity $V_R$ of a Rayleigh surface wave.

4. The method of claim 3 further comprising the step of calculating a shear wave (S-wave) velocity $V_S$ in the test object based on the P-wave velocity and the Rayleigh wave velocity.

5. The method of claim 4 wherein the step of calculating the S-wave velocity further comprises the step of calculating the S-wave velocity $V_S$ in accordance with the following equation $$\left(2 - \frac{v_R^2}{v_S^2}\right)^2 - 4*\left(1 - \frac{v_R^2}{v_P^2}\right)^{\frac{1}{2}}*\left(1 - \frac{v_R^2}{v_S^2}\right)^{\frac{1}{2}} = 0.$$

6. The method of claim 3 wherein the receiving wedge angle is zero, and wherein the calculated P-wave velocity $V_P$ and the calculated Raleigh wave velocity $V_R$ are independent of the wedge velocity $V_W$.

7. The method of claim 3 further including the steps of:
   defining a P-wave region of interest in each of the A-scans, the P-wave region of interest corresponding to approximate P-wave arrival times of P-wave signals generated by the P-type surface wave and being based on at least one nominal P-wave mode property;
   finding a set of P-wave reception delays to be applied to each element (n), wherein, after application of the P-wave reception delays, P-wave time-of-flight measurements from the at least one emitting element of the emitting probe to each element (n) of the receiving probe are equal to a constant P-wave time-of-flight $\tau_P$ for all n from 1 to N; and,
   calculating the P-wave velocity from the set of P-wave reception delays and the known parameters.

8. The method of claim 7 wherein the at least one nominal P-wave mode property is that the P-type surface wave has a high acoustic velocity and comprises earliest received echo signals in the A-scans.

9. The method of claim 7 wherein the set of P-wave reception delays comprises P-wave reception delays which vary linearly as a function of n, and a $n^{th}$ P-wave reception delay is equal to $\varepsilon_P{*}n$ wherein $\varepsilon_P$ is a constant, and wherein the step of calculating the P-wave velocity comprises calculating the P-wave velocity $V_P$ in accordance with the following equation $$\varepsilon_P = \frac{p}{v_w} * \left( \sin\theta_w * \sqrt{1 - \left(\frac{v_w}{v_P}\right)^2} - \left(\frac{v_w}{v_P}\right) * \cos\theta_w \right).$$

10. The method of claim 7 further comprising the step of measuring a separation distance S between a first surface of the emitting wedge and a second surface of the receiving wedge, the measurement being based on the constant P-wave time-of-flight $\tau_P$ and the P-wave velocity $V_P$.

11. The method of claim 10 wherein the first surface and the second surface are perpendicular to the test surface and wherein the step of determining the separation distance S comprises the steps of:
   performing a reference acquisition to measure a reference propagation delay $\tau_0$; and,
   calculating the separation distance S according to the following equation $$S = v_P * (\tau_P - \tau_0).$$

12. The method of claim 11 wherein the step of performing a reference acquisition further comprises the steps of:
   placing the emitting wedge and the receiving wedge at a zero separation distance wherein the first surface is in contact with the second surface;
   firing the at least one emitting element of the emitting probe;
   receiving corresponding A-scans from each element (n) of the receiving probe;
   defining a P-wave region of interest in each of the A-scans;

finding a set of reference reception delays to be applied to each element (n), wherein after application of the reference reception delays a measured reference P-wave time-of-flight from the at least one emitting element of the emitting probe to each element (n) of the receiving probe is a constant reference time-of-flight for all n from 1 to N;

setting the reference propagation delay $\tau_0$ equal to the constant reference time-of-flight; and, placing the emitting wedge and the receiving wedge at the separation distance S, wherein the emitting wedge and the receiving wedge are at locations on the test surface convenient for NDT/NDI of the test object.

13. The method of claim 3 wherein the step of calculating the Rayleigh wave velocity further includes the steps of:

defining a Rayleigh wave region of interest in each of the A-scans, the Rayleigh wave region of interest corresponding to approximate Rayleigh wave arrival times of Rayleigh wave signals generated by the Rayleigh surface wave and being based on at least one nominal Rayleigh wave mode property;

finding a set of Rayleigh reception delays to be applied to each element (n), wherein, after application of the Rayleigh reception delays, a measured Rayleigh wave time-of-flight from the at least one emitting element of the emitting probe to each element (n) of the receiving probe is a constant Rayleigh wave time-of-flight $\tau_R$ for all n from 1 to N; and, calculating the Rayleigh wave velocity from the set of Rayleigh reception delays and the known parameters.

14. The method of claim 13 wherein the at least one nominal Rayleigh wave mode property is that the Rayleigh surface wave has a lower acoustic velocity than the P-type surface wave and that there is an approximately known velocity ratio of the Rayleigh wave velocity to the P-wave velocity, enabling the approximate Rayleigh wave arrival times to be calculated.

15. The method of claim 13 wherein the set of Rayleigh reception delays comprises Rayleigh reception delays which vary linearly as a function of n, and a $n^{th}$ Rayleigh reception delay is equal to $\varepsilon_R*n$ wherein $\varepsilon_R$ is a constant, and wherein the step of calculating the Rayleigh wave velocity comprises calculating the Rayleigh wave velocity $V_R$ in accordance with the following equation $$\varepsilon_R = \frac{p}{v_w} * \left( \sin \theta_w * \sqrt{1 - \left(\frac{v_w}{v_R}\right)^2} - \left(\frac{v_w}{v_R}\right) * \cos \theta_w \right).$$

16. The method of claim 1 wherein the ultrasonic measurement system is an ultrasonic non-destructive testing and inspection (NDT/NDI) system, and the method is activated during a NDT/NDI operation.

17. The method of claim 1 wherein the emitting probe is a single element probe.

18. The method of claim 1 wherein the emitting probe is an array probe.

19. The method of claim 18 wherein the steps of the method are performed twice, a first time with a first probe configured as the emitting probe and a second probe configured as the receiving probe, and a second time with the second probe configured as the emitting probe and the first probe configured as the receiving probe.

20. The method of claim 1 wherein the emitting wedge angle is equal to the receiving wedge angle.

21. An ultrasonic measurement system for measuring ultrasonic velocity, the system comprising:

an emitting probe operable with an emitting wedge and a receiving probe operable with a receiving wedge, wherein the receiving probe is an array probe having a number N of receiving elements, the receiving elements designated element (n) for n=1 to N, and wherein the wedges are configured to be in contact with a test surface of a test object;

a known parameter unit for storing known parameters for the probes and the wedges;

an acquisition unit configured to fire at least one emitting element of the emitting probe, thereby causing the at least one emitting element to emit beams of ultrasonic energy into the emitting wedge, including a critical beam at a critical angle which generates a surface wave propagating near the test surface in the test object towards the receiving wedge, the acquisition unit further configured to receive corresponding A-scans from each element (n) of the receiving probe, the A-scans comprising amplitudes of received echo signals as function of arrival times at each element (n); and, at least one velocity unit configured to determine at least one surface wave velocity of the surface wave, and, wherein the known parameters comprise the number N of the receiving elements, a pitch p, wherein p is the distance between adjacent receiving elements, an emitting wedge angle $\theta_w'$ of the emitting wedge, a receiving wedge angle $\theta_w$ of the receiving wedge, and a wedge velocity $V_w$, wherein $V_w$ is the velocity of longitudinal waves in the receiving wedge.

22. The system of claim 21 wherein the at least one velocity unit is a P-wave velocity unit and the at least one surface wave velocity is a longitudinal wave (P-wave) velocity $V_P$ of a P-type surface wave.

23. The system of claim 21 wherein the at least one velocity unit is a P-wave velocity unit and a Rayleigh wave velocity unit and the at least one surface wave velocity is a longitudinal wave (P-wave) velocity $V_P$ of a P-type surface wave and a Rayleigh wave velocity $V_R$ of a Rayleigh surface wave.

24. The system of claim 23 further comprising a shear wave (S-wave) velocity calculator configured to calculate an S-wave velocity $V_S$ in the test object based on the P-wave velocity and the Rayleigh wave velocity.

25. The system of claim 24 wherein the S-wave velocity calculator is further configured to calculate the S-wave velocity $V_S$ in accordance with the following equation $$\left(2 - \frac{v_R^2}{v_S^2}\right)^2 - 4*\left(1 - \frac{v_R^2}{v_P^2}\right)^{\frac{1}{2}}*\left(1 - \frac{v_R^2}{v_S^2}\right)^{\frac{1}{2}} = 0.$$

26. The system of claim 23 wherein the receiving wedge angle is zero, and wherein the calculated P-wave velocity $V_P$ and the calculated Raleigh wave velocity $V_R$ are independent of the wedge velocity $V_W$.

27. The system of claim 23 wherein the P-wave velocity unit further comprises:

a P-wave region of interest estimator configured to define a P-wave region of interest in each of the A-scans, the P-wave region of interest corresponding to approximate P-wave arrival times of P-wave signals generated by the P-type surface wave and being based on at least one nominal P-wave mode property;

a P-wave delay finding unit configured to find a set of P-wave reception delays to be applied to each element (n), wherein after application of the P-wave reception delays a measured P-wave time-of-flight from the at least one emitting element of the emitting probe to each element (n) of the receiving probe is a constant P-wave time-of-flight $\tau_P$ for all n from 1 to N; and, a P-wave velocity calculator configured to calculate the P-wave velocity from the set of P-wave reception delays and the known parameters.

28. The system of claim 27 wherein the at least one nominal P-wave mode property is that the P-type surface wave has a high acoustic velocity and comprises earliest received echo signals in the A-scans.

29. The system of claim 27 wherein the set of P-wave reception delays comprises P-wave reception delays which vary linearly as a function of n, and a $n^{th}$ P-wave reception delay is equal to $\varepsilon_P*n$ wherein $\varepsilon_P$ is a constant, and wherein the step of calculating the P-wave velocity comprises calculating the P-wave velocity $V_P$ in accordance with the following equation $$\varepsilon_P = \frac{p}{v_w} * \left( \sin \theta_w * \sqrt{1 - \left(\frac{v_w}{v_P}\right)^2} - \left(\frac{v_w}{v_P}\right) * \cos \theta_w \right).$$

30. The system of claim 27 further comprising a probe separation calculator configured to measure a separation distance S between a first surface of the emitting wedge and a second surface of the receiving wedge, wherein the first surface and the second surface are perpendicular to the test surface, and wherein the measurement of the separation distance S is based on the constant P-wave time-of-flight $\tau_P$ and the P-wave velocity $V_P$.

31. The system of claim 30 further comprising a reference acquisition unit configured to determine a reference propagation delay $\tau_0$, wherein the reference acquisition unit comprises:

a zero separation A-scan acquisition unit configured to fire the at least one emitting element of the emitting probe an d to receive corresponding A-scans from each element (n) of the receiving probe;

a reference region of interest estimator configured to define a P-wave region of interest in each of the A-scans;

a reference delay finding unit configured to find a set of reference reception delays to be applied to each element (n), wherein, after application of the reference reception delays, measured reference times of flight from the at least one emitting element of the emitting probe to each element (n) of the receiving probe are a constant reference time-of-flight for all n from 1 to N, and wherein the reference propagation delay $\tau_0$ is equal to the constant reference time-of-flight.

32. The system of claim 31 wherein the probe separation calculator calculates the separation distance S according to the following equation $S = v_P * (\tau_P - \tau_0).$ 33. The system of claim 23 wherein the Rayleigh velocity unit further comprises:

a Rayleigh region of interest estimator configured to define a Rayleigh wave region of interest in each of the A-scans, the Rayleigh wave region of interest corresponding to approximate Rayleigh wave arrival times of Rayleigh wave signals generated by the Rayleigh surface wave and being based on at least one nominal Rayleigh wave mode property;

a Rayleigh delay finding unit configured to find a set of Rayleigh reception delays to be applied to each element (n), wherein after application of the Rayleigh reception delays a measured Rayleigh wave time-of-flight from the at least one emitting element of the emitting probe to each element (n) of the receiving probe is a constant Rayleigh time-of-flight $\tau_R$ for all n from 1 to N;

a Rayleigh velocity calculator configured to calculate the Rayleigh wave velocity from the set of Rayleigh reception delays and the known parameters.

34. The system of claim 33 wherein the at least one nominal Rayleigh wave mode property is that the Rayleigh surface wave has a lower acoustic velocity than the P-type surface wave and that there is an approximately known velocity ratio of the Rayleigh wave velocity to the P-wave velocity, enabling the approximate Rayleigh wave arrival times to be calculated.

35. The system of claim 33 wherein the set of Rayleigh reception delays comprises Rayleigh reception delays which vary linearly as a function of n, and a $n^{th}$ Rayleigh reception delay is equal to $\varepsilon_R*n$ wherein $\varepsilon_R$ is a constant, and wherein the step of calculating the Rayleigh wave velocity comprises calculating the Rayleigh wave velocity $V_R$ in accordance with the following equation $$\varepsilon_R = \frac{p}{v_w} * \left( \sin \theta_w * \sqrt{1 - \left(\frac{v_w}{v_R}\right)^2} - \left(\frac{v_w}{v_R}\right) * \cos \theta_w \right).$$

36. The system of claim 21 wherein the ultrasonic measurement system is an ultrasonic non-destructive testing and inspection (NDT/NDI) system, and the method is activated during a NDT/NDI operation.

37. The system of claim 21 wherein the emitting probe is a single element probe.

38. The system of claim 21 wherein the emitting probe is an array probe.

39. The system of claim 38 wherein the acquisition unit is further configured to acquire A-scans a first time with a first probe configured as the emitting probe and a second probe configured as the receiving probe, and a second time with the second probe configured as the emitting probe and the first probe configured as the receiving probe.

40. The system of claim 21 wherein the emitting wedge angle is equal to the receiving wedge angle.

* * * * *